United States Patent
Tang (10) Patent No.: US 7,090,657 B2
(45) Date of Patent: Aug. 15, 2006

(54) AUTO-DISABLE SAFETY SYRINGE

(75) Inventor: Zengji Tang, Jiangxi Province (CN)

(73) Assignee: Jiangxi Hongda Medical Equipment Group Ltd. Co., Jiangxi Pronivce (CH)

( * ) Notice: Subject to any disclaimer, the term of this patent is extended or adjusted under 35 U.S.C. 154(b) by 77 days.

(21) Appl. No.: 10/849,015

(22) Filed: May 20, 2004

(65) Prior Publication Data
US 2004/0236283 A1    Nov. 25, 2004

(30) Foreign Application Priority Data
May 21, 2003   (CN) ............................... 03 1 28859

(51) Int. Cl.
*A61M 5/00*     (2006.01)
*A61M 5/315*    (2006.01)
(52) U.S. Cl. ...................... 604/110; 604/218
(58) Field of Classification Search ............. None
See application file for complete search history.

(56) References Cited

U.S. PATENT DOCUMENTS 5,401,246 A * 3/1995 Mazur et al. ................ 604/110
6,129,711 A * 10/2000 Speck ......................... 604/199

* cited by examiner

*Primary Examiner*—Michael J. Hayes
(74) *Attorney, Agent, or Firm*—Jacobson Holman PLLC (57) ABSTRACT

An auto-disable safety syringe including a needle, a needle seat, a plunger, and a barrel. A cover of a needle seat chamber formed in the needle seat is provided with a splined hole having teeth and grooves. The needle seat has a ring block and an outer wall with splined teeth capable of passing through the grooves. A locking groove is formed in an inner cavity of the ring block and a locking head is formed on a connecting head to form a locking mechanism. Spiral grooves on the inner cavity engage with protrusions on the connecting head. When the locking head and the locking groove are interlocked and the plunger is retracted, the needle seat and the needle are retracted inside the barrel together. The syringe protects both patient and medical staff, is simple in structure, convenient to use and destructible.

16 Claims, 9 Drawing Sheets

AUTO-DISABLE SAFETY SYRINGE

BACKGROUND OF THE INVENTION

1. Field of the Invention

The present invention generally relates to a syringe, and more particularly, to an auto-disable safety syringe having a barrel and a needle seat, in which the needle seat of the syringe can be not only engaged securely with the barrel but also released easily from the barrel of the syringe so as to allow a needle being fully retracted inside the barrel by a plunger, so that the needle is prevented from pricking, scratching or other harmful exposure to medical staffs during subsequent handling of the self-destructed syringe, thus achieving a dual protection of patients and medical staffs.

2. Background of the Related Art

Medically, a disposable syringe is widely used in order to avoid cross contaminations. Conventionally, a medical staff breaks a plunger of the disposable syringe after an injection so as to achieve the disposable purpose. However, the auto-disable syringe still tends to prick or scratch the medical staff during its subsequent handling, this may cause a further contamination, so that the conventional disposable syringe could not achieve a "dual protection", that is, the conventional syringe could not protect both medical staffs and patients simultaneously.

Recently, for protecting both medical staffs and patients, there have been proposed safety syringes, some of which have been filed for patents, such syringes employ a structure with a manually retractable needle. With the structure, a plunger and a needle seat are connected and interlocked with each other after an injection of syringe, then both the needle seat and the needle are retracted inside the barrel by the plunger when the plunger is manually drawn back. This structure could prevent the used needle from pricking the medical staff. However, the above safety syringe with a manually retractable needle has a problem in connection between the needle seat and the barrel. Conventionally, the needle seat is connected to the barrel by a rubber ring, or an interference fit between a convex ring, a boss or a convex hoop formed integrally on a needle assembly or the needle seat and a certain portion of the barrel. The above connection should be firm and could not be too firm, if the connection is too firm, the needle seat may not be pulled inside the barrel after injection and during destruction, if the connection is not sufficient firm, the injectant may be leaked out and the needle may be automatically retracted during injection, the automatic retraction of the needle will cause that the injection could not be performed. In the prior art, there is provided a syringe in which the needle seat is provided with thread, the needle seat is securely connected to a barrel of the syringe through threaded engagement therebetween, however, in order to release the needle seat from the barrel, the threaded engagement must be manually released directly or indirectly, so that the releasing operation depends on the subjective consciousness of an operator, then there may be a hidden trouble that the syringe is not destructed after use, that is, the syringe is not disposable. Meanwhile, the needle provided with thread is not a standard needle, thus causing the medical staff inconvenient to change needles during use.

In a word, it is in urgent need of providing a safety syringe which can protect both medical staffs and patients simultaneously.

SUMMARY OF THE INVENTION

An object of the present invention is to provide an auto-disable safety syringe to mitigate or obviate the aforementioned problems, the auto-disable syringe of the present invention has a simple structure, is convenient to use and destructive, in which a needle seat of the syringe can be not only connected securely to a barrel of the syringe but also released easily from the barrel to allow a needle being fully retracted inside the barrel by a plunger, thus achieving dual-protection of the medical staffs and patients simultaneously.

The above object of the present invention is achieved by providing an auto-disable safety syringe, comprising a needle; a needle seat connected to the needle; a seal; a plunger; a piston connected to one end of the plunger; a barrel, the plunger and the piston being capable of fitting and reciprocating inside the barrel, the barrel being formed at a bottom end thereof with an ellipse-shape finger grip, a needle seat chamber being formed in front of a large top cover provided at a top end of the barrel, a small top cover formed at a top end of the needle seat chamber being provided with a splined hole, the splined hole being provided with plural protruding teeth on an inner wall thereof, and grooves of the splined hole being formed between adjacent protruding teeth respectively; and a plunger positioning plate capable of fitting over the finger grip of the barrel, the needle seat is formed with a conical fitting and a ring block at a front end and a rear end thereof respectively, the needle seat is formed on an outer wall thereof with splined teeth capable of passing through the grooves, and a neck for embedding the seal is formed between the splined teeth and the ring block.

Preferably, a limit boss is provided on each protruding teeth for limiting a rotation angle of the needle seat, and a slope having a locking angle is formed at a bottom portion of each splined tooth.

Further, a locking groove is provided at a top end of an inner cavity of the ring block, the inner cavity is formed with spiral grooves in an inner wall thereof, a connecting head of the plunger is formed at a top end thereof with a locking head which forms a locking mechanism together with the locking groove, and the connecting head is provided on a side wall thereof with protrusions for engaging with the spiral grooves respectively.

In addition, two plunger positioning plates of semi-ellipse shape are fit over the finger grip of the barrel, the plunger positioning plates are each provided with T-shape grooves respectively, a cross groove is formed by the T-shape grooves when the two plunger positioning plates match each other to fit over the finger grip, and the cross groove limits the plunger to only move linearly inside the barrel.

Preferably, the piston is formed in the form of a seal plate of the plunger or combination of a piston head with a piston ring of the plunger, and one or more piston grooves, in which the piston ring is embedded, are formed in a side wall of the piston head.

Moreover, the rotation angle of the needle seat is set within a limit of 90° by the limit boss, the locking angle of the slope is within a range of 0–25°. Further, the splined hole is provided with one or more grooves, the needle seat is provided on the outer wall thereof with one or more splined teeth which are capable of passing through the grooves and whose shapes are consistent with that of the grooves, and axial shapes of the grooves and the splined teeth are one selected from a group consisted of triangle, rectangle, oblong, trapezoid, sector and semicircle.

In addition, the inner cavity of the ring block is provided at the inner wall thereof with one or more spiral grooves, the connecting head is provided at the side wall thereof with one or more protrusions, and cross sections of the spiral grooves and the protrusions have one shape selected from a group consisted of triangle, rectangle, oblong, trapezoid, sector and semicircle.

Preferably, a stop sheet capable of being torn is formed at a rear portion of the plunger.

In the present invention, since the small top cover of the needle seat chamber is provided with a splined hole, protruding teeth, and grooves, the needle seat is provided at the outer wall thereof with splined teeth capable of passing through the grooves, the neck in which the seal is embedded is formed between the splined teeth and the ring block, and the protruding teeth are each provided with a limit boss thereon, after the needle seat is slid into the needle seat chamber of the barrel, the splined teeth are passed through the grooves of the spline hole, then the needle seat is rotated rightward until it is stopped by the limit boss, at this time, the respectively, and the splined teeth are engaged circumferentially with the limit boss respectively, in addition, the splined teeth are each provided at the bottom portion thereof with a slope having a locking angle, so that the slope at the bottom portion of the splined teeth tightens the engagement between the small top cover of the needle seat chamber, the seal and the needle seat as the rotation angle of the needle seat increases, thus achieving both sealing of the barrel and secure engagement of the needle seat with the barrel. In addition, the ring block at the rear end of the needle seat is fitted in the barrel with a clearance therebetween, so that the needle seat can enter and retreat from the splined hole easily, therefore, it is easy to assemble the syringe and to retract the needle seat.

According to the present invention, the ring block is provided at the inner wall thereof with spiral grooves, the connecting head of the piston is provided at the side wall thereof with protrusions for engaging with the spiral grooves, the spiral grooves and the protrusions form a spiral mechanism which employs a single thread or multiplex thread structure, when the plunger is moved linearly, the protrusions enter the spiral grooves, thus causing the needle seat to rotate in the reverse direction, the splined teeth on the needle seat return to their positions where the splined teeth and the protruding teeth of the splined hole formed on the small top cover of the needle seat chamber are not offset from each other, at this time, the splined teeth can pass through the grooves of the splined hole. While the needle seat is rotated in the reverse direction to its designated position, the locking head of the plunger reaches its designated position and is inserted into the locking groove of the needle seat, thus being interlocked integrally with each other, the locking head and the locking groove form a locking mechanism, when the plunger is retracted, the needle seat and the needle will be drawn to retract inside the barrel together. Then, the plunger is pushed back toward the top of the barrel, so that the needle is pressed into a spiral shape and destroyed. Finally, the plunger is broken, so that the syringe is destroyed and not reusable, therefore, the syringe of the present invention can provide protection of both patient and medical staff.

In the present invention, the needle seat, the needle seat chamber and the seal are universal, the needle seat assembly consisted of the above three elements has two types, i.e. Luer needle seat and Luer-Lock needle seat, the syringe can be constructed as central needle syringe and eccentric needle syringe by mounting the needle seat such that the central line of the needle seat is coincided with or offset from that of the barrel, respectively. The syringe can be also constructed as two-part syringe and three-part syringe by using different pistons.

The present invention has the following advantages:

1. The structure of the syringe is simple, the sealing is secured, and the needle seat may be connected securely to the barrel.
2. The needle is standard so that the syringe is convenient to use.
3. The medical staff can release the needle seat from the barrel through conventional operation without additional operations, and retract the needle seat together with the needle inside the barrel so as to destroy the syringe, thus achieving the disposableness of the syringe.
4. The present invention may be constructed as two-part or three part, central or eccentric, Luer or Luer-Lock needle seat auto-disable safety syringe.

Therefore, the syringe of the present invention can protect both medical staffs and patients simultaneously, avoid cross contaminations, and prevent the used needle from pricking or scratching, thereby infecting the medical staff, so that the present invention provides a novel safety syringe.

BRIEF DESCRIPTION OF THE DRAWINGS

These and/or other aspects and advantages of the invention will become apparent and more readily appreciated from the following description of the preferred embodiments, taken in conjunction with the accompanying drawings of which.

DETAILED DESCRIPTION OF THE PREFERRED EMBODIMENT

The preferred embodiment of the present invention will be described in detail with reference to the drawings, examples of which are illustrated in the drawings, wherein like reference numerals refer to like elements throughout.

Embodiment 1: Two-part Type Auto-disable Safety Syringe with a Central Needle and a Luer-lock Conical Fitting of a Needle Seat With reference to FIG. 1 to FIG. 12, FIG. 1 is a schematic structural view of a two-part type auto-disable safety syringe with a central needle and a Luer-lock conical fitting of a needle seat according to the first embodiment of the present invention, the auto-disable safety syringe comprises a needle 1, a needle seat 2, a seal 3, a piston 4, a plunger 5, a barrel 6, and plunger positioning plates 7, a finger grip 69 is integrally formed at a rear end (bottom end in FIG. 1 and FIG. 2) of the barrel 6.

Figure 2:
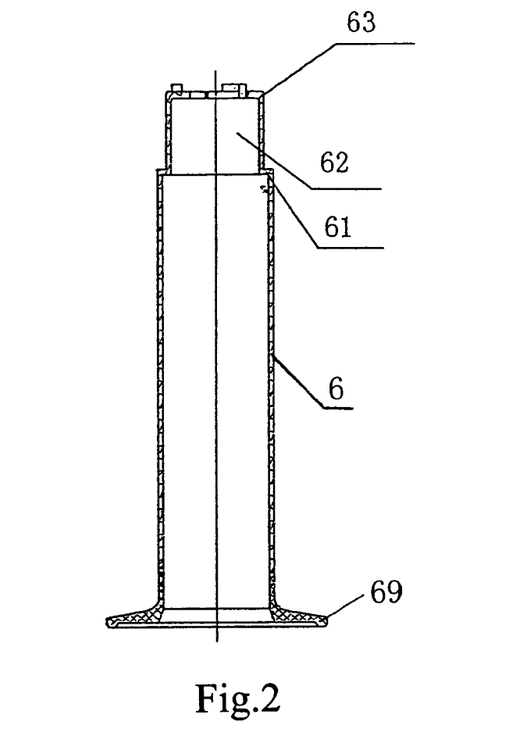
FIG. 2 is a schematic structural view of the barrel of the auto-disable safety syringe according to the first embodiment of the present invention.
Figure 3:
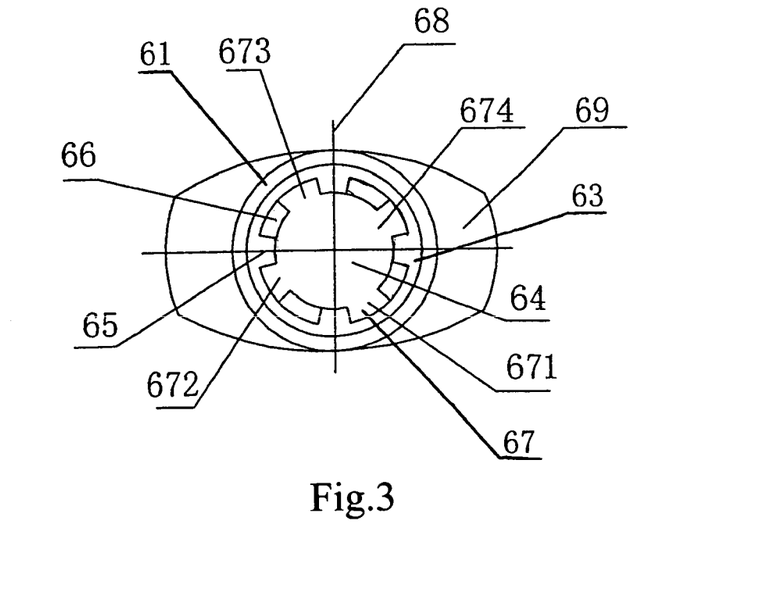
FIG. 3 is a plane view of FIG. 2.

FIG. 2 is a schematic structural view of the barrel of the auto-disable safety syringe according to the first embodiment of the present invention, and FIG. 3 is a plane view of FIG. 2, a cylindrical needle seat chamber 62 is formed in front of a large top cover 61 provided at a front end (top end in FIG. 2) of the barrel 6, the central line of the needle seat chamber 62 is coincided with that of the barrel 6, that is, the barrel 6 is coaxial with the needle seat chamber 62. A small top cover 63 is formed integrally at a top end of the needle seat chamber 62, the small top cover 63 is formed centrally with a splined hole 64, as shown in FIG. 3, plural protruding teeth 65 of the splined hole 64 are provided on the inner wall of the splined hole 64. There is provided a limit boss 66 on each protruding teeth 65 for limiting the rotation angle of the needle seat 2, grooves 67 of the splined hole 64 are formed between adjacent protruding teeth 65, in the present embodiment, there are provided four grooves 671, 672, 673 and 674. The needle seat 2 is formed integrally at a front end thereof with a Luer-Lock conical fitting 26, and with a ring block 22 at a rear end thereof, the Luer-Lock conical fitting 26 can pass through the splined hole 64. The needle seat 2 are formed integrally on an outer wall thereof with splined teeth 21 which can pass through the grooves 67, a neck 25 is formed between the splined teeth 21 and the ring block 22 so as to be embedded with the seal 3. The number of the splined teeth 21 is identical with that of the grooves 67 of the splined hole 64, that is, there are four splined teeth 211, 212, 213 and 214 in the present embodiment, preferably, a slope having a locking angle 28 is formed at the bottom portion of each splined tooth 21, as shown in FIG. 5.

Figure 4:
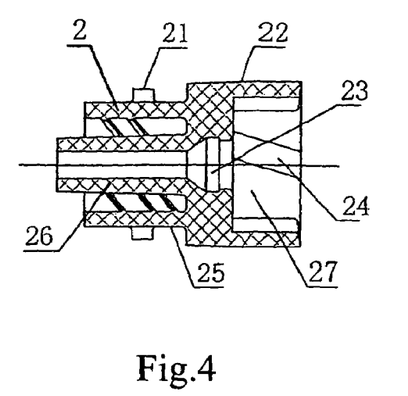
FIG. 4 is a sectional view of the needle seat having the Luer-lock conical fitting according to the first embodiment of the present invention.
Figure 5:
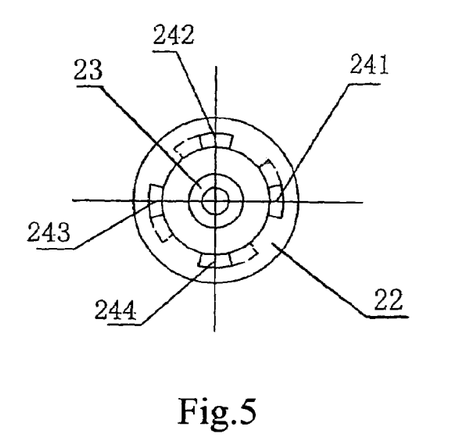
FIG. 5 is a right view of FIG. 4.
Figure 6:
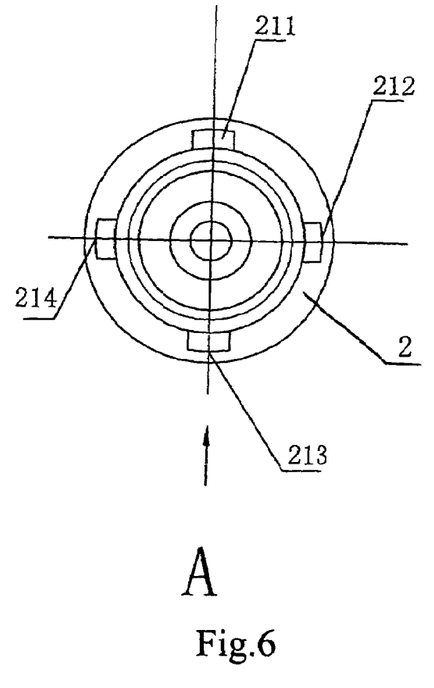
FIG. 6 is a left view of FIG. 4.
Figure 7:
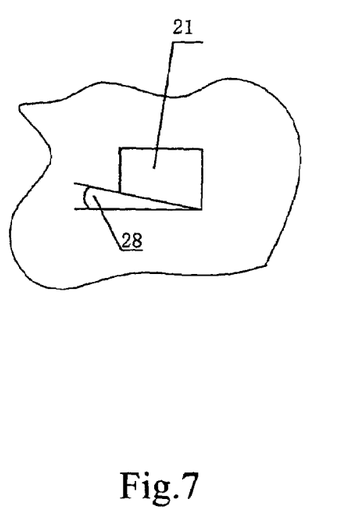
FIG. 7 is a view of a splined tooth in direction A.
Figure 9:
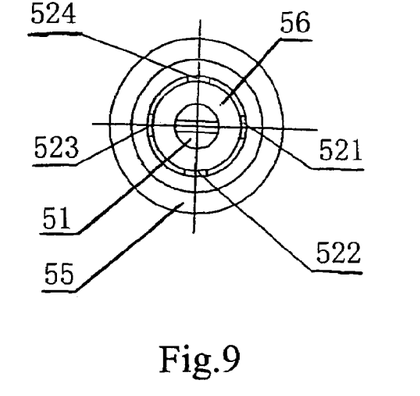
FIG. 9 is a plane of FIG. 8.

As shown in FIGS. 4 and 5, a locking groove 23 is provided in front of the top end of an inner cavity 27 of the ring block 22, and the inner cavity 27 is provided with spiral grooves 24 in the inner wall thereof, the piston 4 is formed in the form of a sealing plate 55 of the plunger 5, a locking head 51 is formed at a top end of a connecting head 56 of the plunger 5, the locking head 51 and the locking groove 23 form a locking mechanism, the connecting head 56 is provided on the side wall thereof with protrusions 52 for engaging with the spiral grooves 24 respectively. The spiral grooves 24 are formed in the form of four-head dextral female thread grooves 241, 242, 243 and 244, the protrusions 52 are formed in the form of four-head male thread columns 521, 522, 523 and 524, as shown in FIG. 9.

Figure 8:
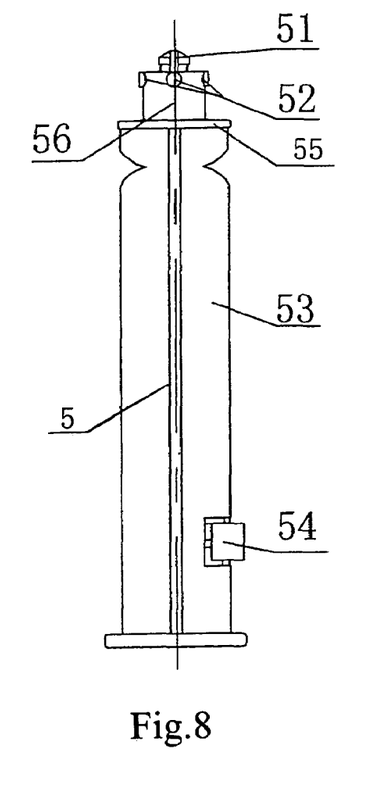
FIG. 8 is a structural view of a plunger according to the first embodiment of the present invention.

A square stop sheet 54 is formed at a rear portion of one of body pieces 53 of the plunger 5, the stop sheet 54 could be torn off from the plunger 5 by hand.

Figure 1:
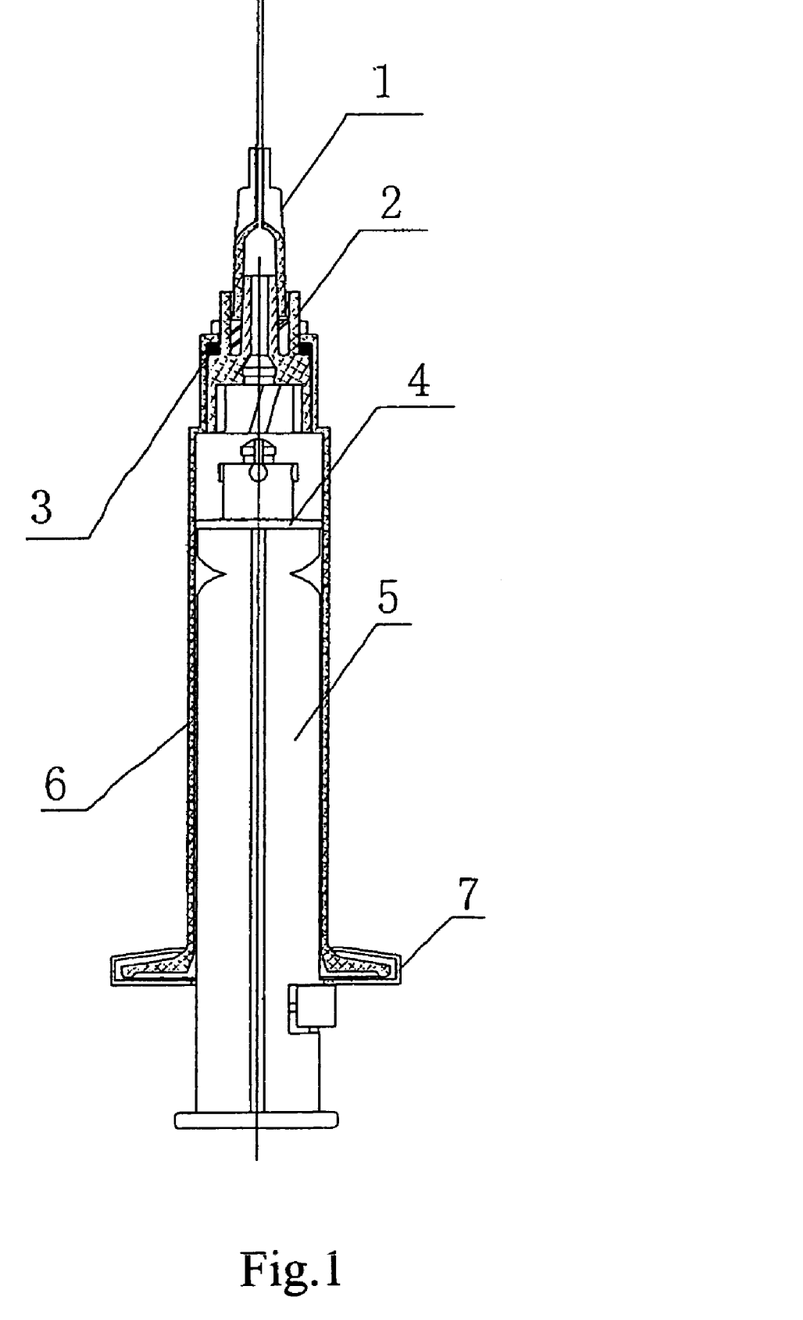
FIG. 1 is a schematic structural view of a two-part type auto-disable safety syringe with a central needle and a threaded Joint of a needle seat according to the first embodiment of the present invention.
Figure 10:
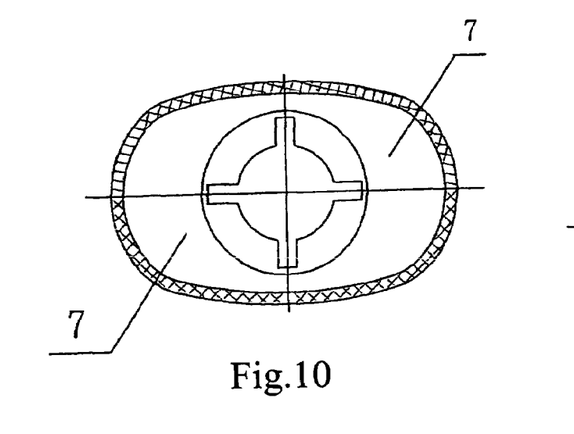
FIG. 10 is a schematic structural view of two plunger positioning plates in a matching state according to the first embodiment of the present invention.
Figure 11:
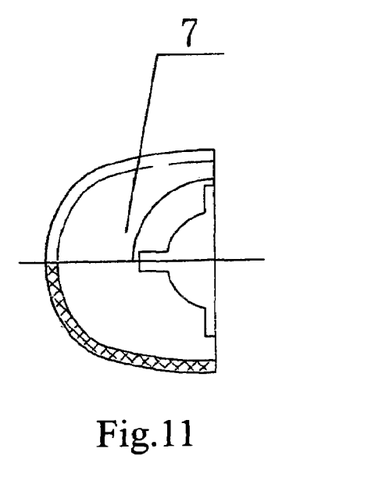
FIG. 11 is a half section view of one of the two positioning plates.

As shown in FIGS. 1, 10 and 11, two plunger positioning plates 7 of semi-ellipse shape are fit over the finger grip 69, the plunger positioning plates 7 are each provided with T-shape grooves respectively, a cross groove is formed by the T-shape grooves when the two plunger positioning plates 7 match each other to fit over the finger grip 69, the cross groove is used to limit the plunger to be only moved linearly inside the barrel 6.

The rotation angle of the needle seat 2 is set within the limit of 90° by the limit bosses 66, the splined teeth 21 are each formed with a slope at the bottom portion thereof, the locking angle 28 of the slope is within the range of 0–25°.

The axial shape of the grooves 67 and the splined teeth 21 is one selected from a group consisted of triangle, rectangle, oblong, trapezoid, sector and semicircle, respectively. The cross section of the spiral grooves 24 and the protrusions 52 has one shape selected from a group consisted of triangle, rectangle, oblong, trapezoid, sector and semicircle, respectively.

The assembling of the syringe of the present embodiment is described as follows.

Firstly, the seal 3 is fit over the neck 25 of the needle seat 2, the needle seat 2 is slid into the needle seat chamber 62 of the barrel 6, the splined teeth 21 are passed through the grooves 67 of the splined hole 64, then the needle seat 2 is rotated rightward until the splined teeth 21 touch the limit bosses 66, so that the needle seat 2 could not be rotated further, at this time, the splined teeth 21 are offset from and overlap the protruding teeth 65 of the splined hole 64, so as to engage circumferentially with the limit bosses 66, respectively. The splined teeth 21 are each provided at the bottom portion thereof with a slope having the locking angle 28 of 0–25°, therefore, as the rotation angle of needle seat 2 increases, the engagement between the small top cover 63 of the needle seat chamber 62, the seal 3 and needle seat 2 will become tighter and tighter, so that the needle seat 2 is engaged securely with the barrel 6. Sequentially, the two-part type plunger 5 is mounted, any one of the body pieces 53 of the plunger 5 is kept in a direction corresponding to the direction of a short axis 68 of the finger grip 69 of the barrel 6, and the stop member 54 formed at the rear portion of the plunger is outside of the finger grip 69 of the barrel 6, the two plunger positioning plates 7 are fit over the finger grip 69, the plunger 5 is pushed until the stop member 54 just touches the plunger positioning plates 7.

Figure 12:
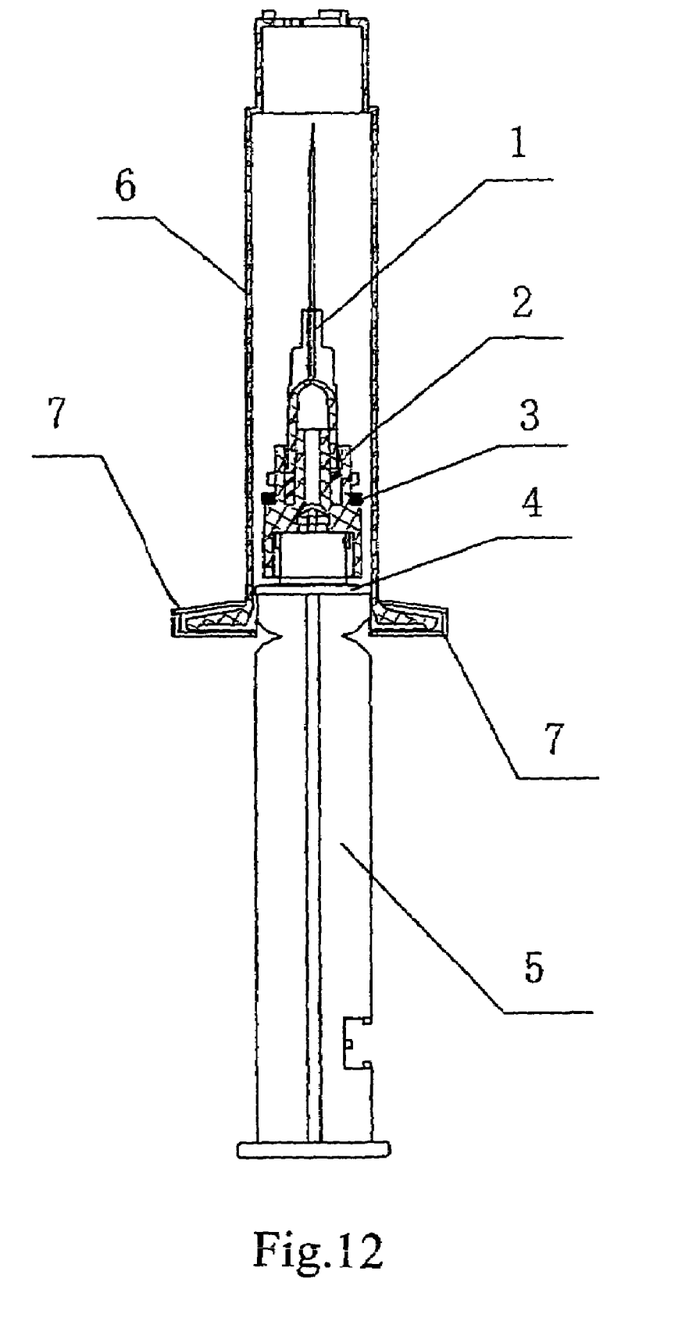
FIG. 12 is a schematic state view of a two-part type auto-disable safety syringe with a central needle and a Luer-lock conical fitting of a needle seat after it finishes an injection.
Figure 13:
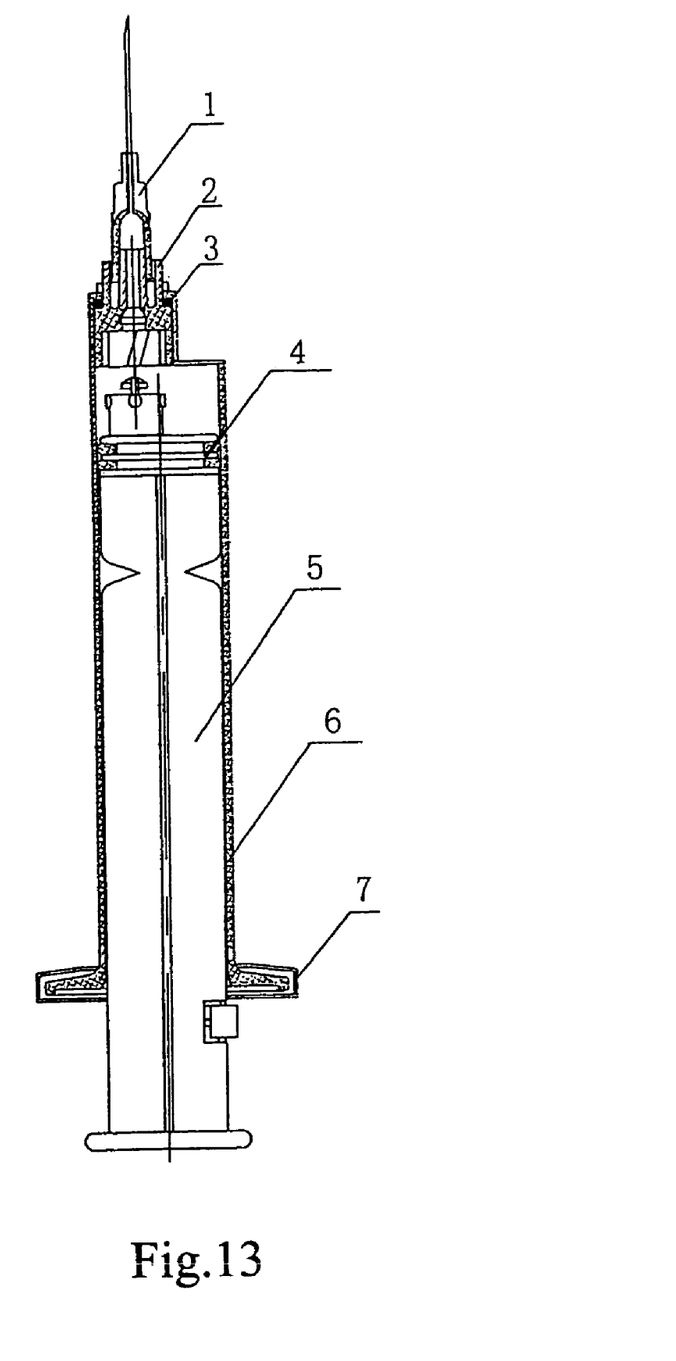
FIG. 13 is a schematic structural view of a three-part type auto-disable safety syringe with an eccentric needle and a Luer conical fitting of a needle seat according to the second embodiment of the present invention.

In use, the stop sheet 54 is first torn off by hand, so that the syringe could be used in a conventional manner. During the whole injection, the plunger 5 is limited to only move linearly parallel to the central line of the barrel 6 due to the plunger positioning plates 7, when the injection approaches finishing, the four columns 521, 522, 523 and 524 on the plunger 5 will be engaged with the four spiral grooves 241, 242, 243 of the needle seat 2, respectively. As the plunger 5 is pushed, the protrusions 52 of the plunger 5 will cause the needle seat 2 to rotate in a reverse direction, the splined teeth 21 and the protruding teeth 65 of the splined hole 64 will return to a non-offset state, while the needle seat 2 is rotated in the reverse direction to its designated position, the locking groove 23 of the needle seat 2 and the locking head 51 of the plunger 5 will reach its designated positions and interlocked integrally with each other respectively, when the plunger 5 is retracted, the needle seat 2 and the needle will be drawn to retract inside the barrel 6 together, As shown in FIG. 12. Then, the plunger 5 is pushed back toward the top of the barrel, so that the needle 1 is pressed into spiral shape. Finally, the plunger 5 is broken, so that the syringe is destroyed and not reusable.

Embodiment 2: Three-part Type Auto-disable Safety Syringe with an Eccentric Needle and a Luer Conical Fitting of a Needle Seat The needle 1, the needle seat 2, the seal 3, the plunger 5, the barrel 6, and the plunger positioning plates 7 in the embodiment 2 are identical with that in the embodiment 1, so that the detail descriptions thereof are omitted here, the embodiment 2 is different from the embodiment 1 in the following.

In the embodiment 2, as shown in FIG. 13–FIG. 21, the barrel 6 of the syringe has an eccentric head portion, the central line of the needle seat chamber 62 of the barrel 6 is parallel to that of the barrel 6 and positioned on the short axis 68 of the finger grip 69 of the barrel 6.

Figures 14, 15, 16, 17, 18:
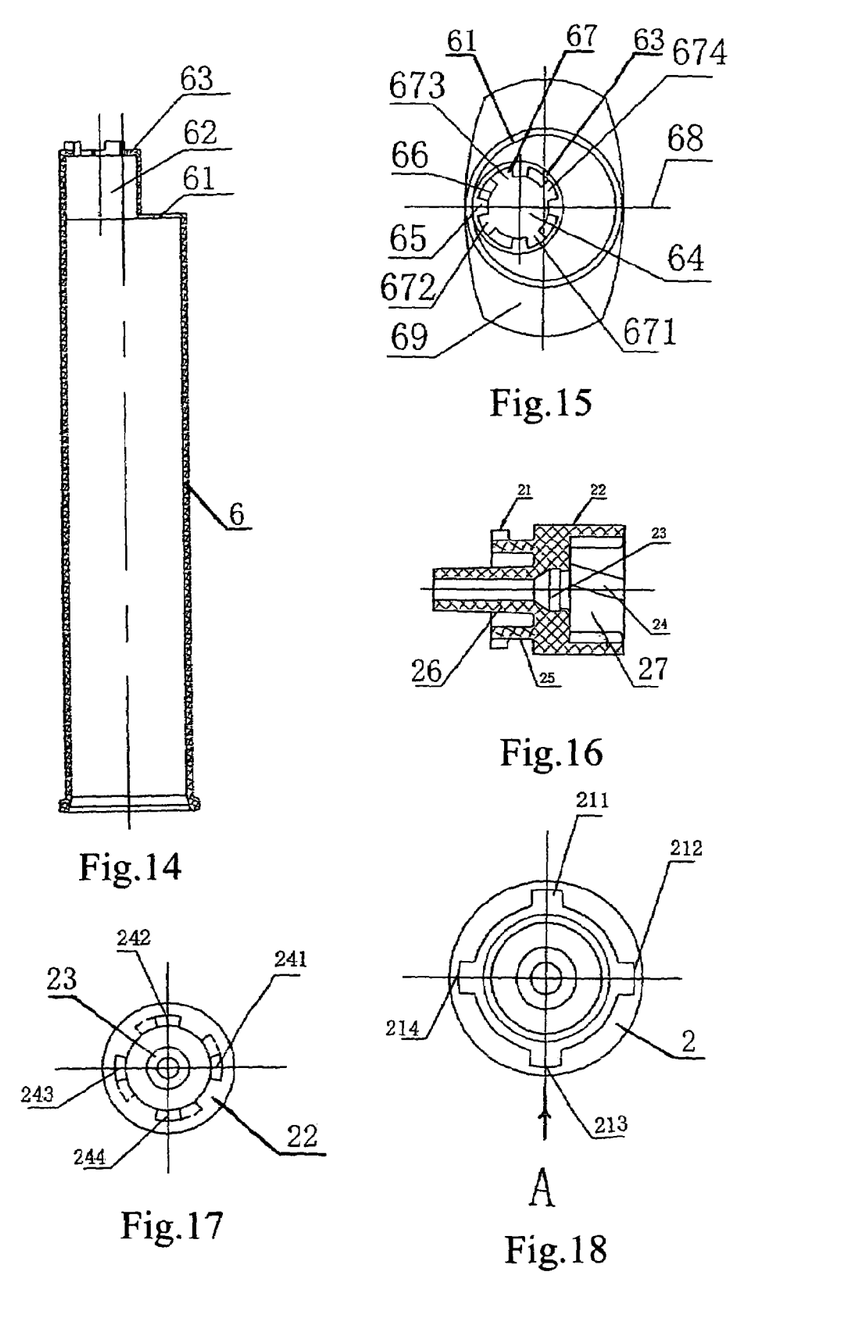
FIG. 14 is a schematic structural view of a barrel of the auto-disable safety syringe according to the second embodiment of the present invention.
FIG. 15 is a plane view of FIG. 14.
FIG. 16 is a sectional view of a needle seat having a Luer conical fitting according to the second embodiment of the present invention.
FIG. 17 is a right view of FIG. 16.
FIG. 18 is a left view of FIG. 16.

The fitting 26 formed at front end of the needle seat 2 is a Luer conical fitting.

Figure 19:
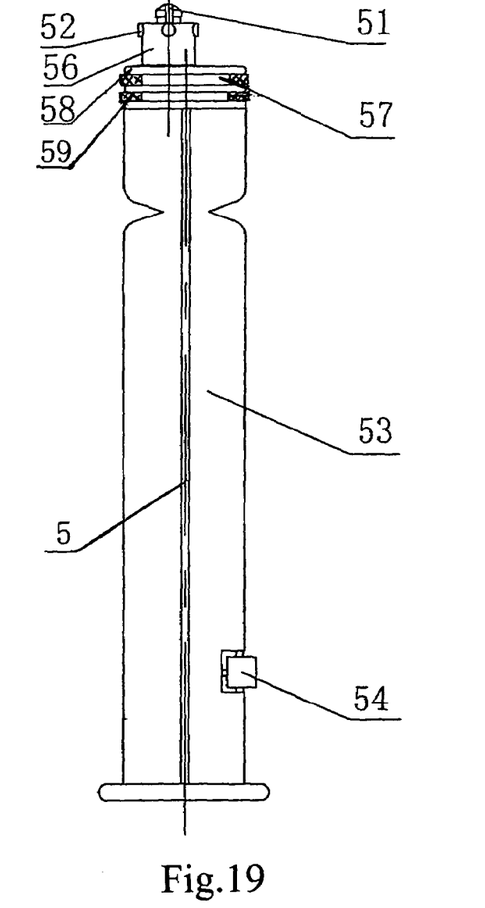
FIG. 19 is a structural view of a plunger according to the second embodiment of the present invention.
Figure 20:
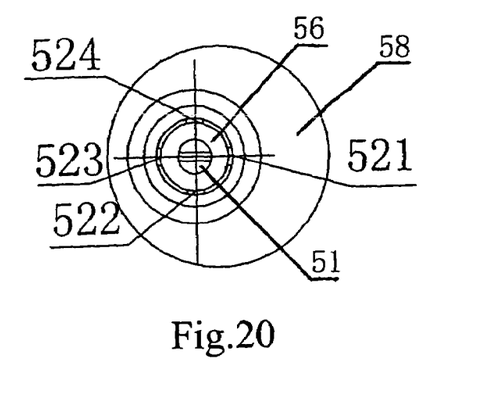
FIG. 20 is a plane of FIG. 19.
Figure 21:
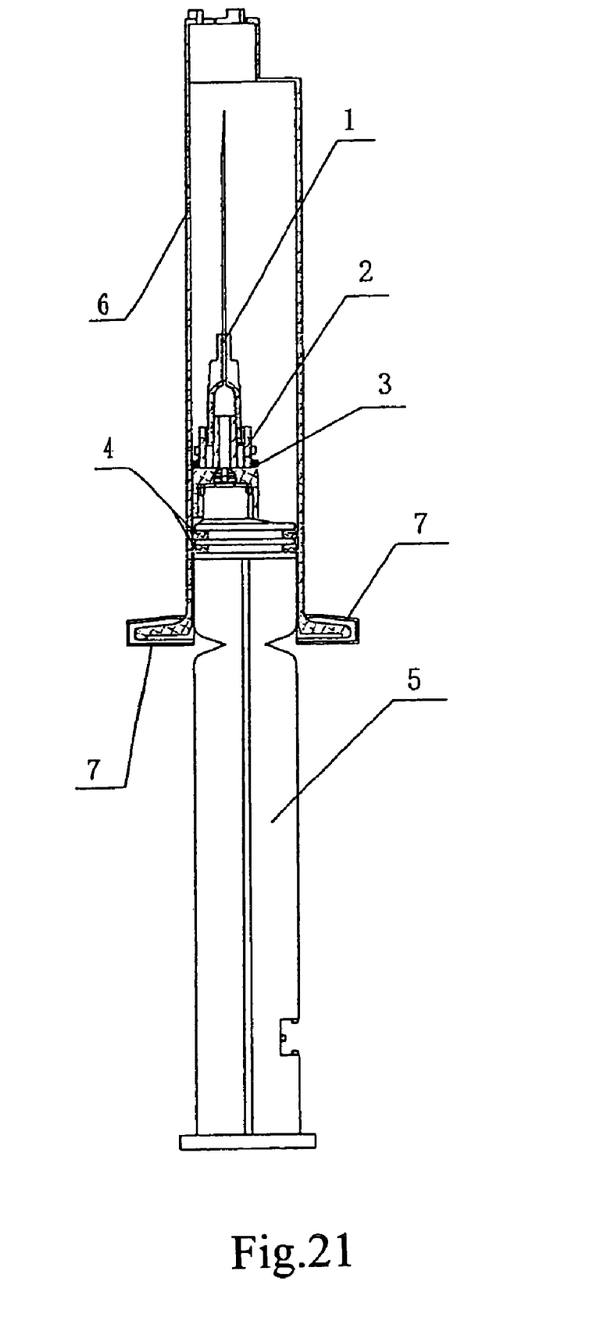
FIG. 21 is a schematic state view of a three-part type auto-disable safety syringe with an eccentric needle and a Luer conical fitting of a needle seat after it finishes an injection.

The piston 4 is formed by combination of a piston head 58 with piston rings 59 of the plunger 5, two piston grooves 57 are formed in the side wall of the piston head 58, in which the piston rings 59 are embedded respectively.

The assembling and use of the syringe according to the embodiment 2 are identical with that according to the embodiment 1.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An auto-disable safety syringe, comprising:
    a needle;
    a needle seat connected to said needle;
    a seal;
    a plunger;
    a piston connected to one end of said plunger;
    a barrel, said plunger and said piston being capable of fitting and reciprocating inside said barrel, said barrel being formed at a bottom end thereof with a finger grip, a needle seat chamber being formed in front of a large top cover provided at a top end of said barrel, a small top cover formed at a top end of said needle seat chamber being provided with a splined hole, said splined hole being provided with plural protruding teeth on an inner wall thereof, and grooves of said splined hole being formed between adjacent protruding teeth respectively;
    a plunger positioning plate capable of fitting over said finger grip of said barrel;
    said needle seat being formed with a conical fitting and a ring block at a front end and a rear end thereof respectively, said needle seat being formed on an outer wall thereof with splined teeth capable of passing through said grooves, and a neck for embedding said seal being formed between said splined teeth and said ring block; and
    a locking groove being provided at a top end of an inner cavity of said ring block, said inner cavity being formed with spiral grooves in an inner wall thereof, a connecting head of said plunger being formed at a top end thereof with a locking head which forms a locking mechanism together with said locking groove, and said connecting head being provided on a side wall thereof with protrusions for engaging with said spiral grooves respectively.

2. The auto-disable safety syringe according to claim 1, wherein a limit boss is formed on each protruding tooth for limiting a rotation angle of said needle seat, and a slope having a locking angle is formed at a bottom portion of each tooth.

3. The auto-disable safety syringe according to claim 2, wherein said rotation angle of said needle seat is set within a limit of 90° by said limit boss, said locking angle of the slope being within a range of 0–25°.

4. The auto-disable safety syringe according to claim 3, wherein a stop sheet capable of being torn is formed at a rear portion of said plunger.

5. The auto-disable safety syringe according to claim 1, wherein two plunger positioning plates of semi-ellipse shape are fit aver said finger grip of said barrel, said plunger positioning plates each being provided with T-shape grooves respectively, a cross groove being formed by said T-shape grooves when said two plunger positioning plates match each other to fit over said finger grip, and said cross groove limiting said plunger to be only moved linearly inside said barrel.

6. The auto-disable safety syringe according to claim 5, wherein said splined hole is provided with one or more grooves, said needle seat being provided on the outer wall thereof with one or more splined teeth which are capable of passing through said grooves and whose shapes are consistent with that of said grooves, and axial shapes of said grooves and said splined teeth being selected from the group consisting of triangle, rectangle, oblong, trapezoid, sector and semicircle.

7. The auto-disable safety syringe according to claim 6, wherein said inner cavity of the ring block is provided at the inner wall thereof with one or more spiral grooves, said connecting head being provided at the side wall thereof with one or more protrusions, and cross sections of said spiral grooves and said protrusions having a shape selected from the group consisting of triangle, rectangle, oblong, trapezoid, sector and semicircle.

8. The auto-disable safety syringe according to claim 7, wherein said piston includes a seal plate of said plunger or combination of a piston head with a piston ring of said plunger, and one or more piston grooves, in which said piston ring is embedded, are formed in a side wall of said piston head.

9. An auto-disable safety syringe, comprising:
    a needle;
    a needle seat connected to said needle;
    a seal;
    a plunger;
    a piston connected to one end of said plunger;
    a barrel, said plunger and said piston being capable of fitting and reciprocating inside said barrel, a needle seat chamber being formed in front of a first cover provided at a top end of said barrel, a second cover provided with a splined hole being formed at a top end of said needle seat chamber, said splined hole having teeth and grooves on an inner wall thereof;

said needle seat being formed with a ring block at a rear end thereof, an outer wall of said needle seat having splined teeth capable of passing through said grooves; and a locking groove being provided at a top end of an inner cavity of said ring block, said inner cavity being formed with spiral grooves in an inner wall thereof, a connecting head of said plunger being formed at a top end thereof with a locking head which forms a locking mechanism together with said locking groove, and said connecting head being provided on a side wall thereof with protrusions for engaging with said spiral grooves respectively.

10. The auto-disable safety syringe according to claim 9, wherein a limit boss is formed on each of said teeth for limiting a rotation angle of said needle seat, and a slope having a locking angle is formed at a bottom portion of each tooth.

11. The auto-disable safety syringe according to claim 10, wherein said rotation angle of said needle seat is set within a limit of 90° by said limit boss, said locking angle of the slope being within a range of 0–25°.

12. The auto-disable safety syringe according to claim 9, further comprising a finger grip formed on said barrel and two plunger positioning plates fit over said finger grip, said plunger positioning plates each being provided with respective T-shape grooves, a cross groove being formed by said T-shape grooves when said two plunger positioning plates match each other to fit over said finger grip, and said cross groove limiting said plunger to be only moved linearly inside said barrel.

13. The auto-disable safety syringe according to claim 12, wherein said splined hole is provided with one or more grooves, said needle seat being provided on the outer wall thereof with one or more splined teeth which are capable of passing through said grooves, and axial shapes of said grooves and said splined teeth being selected from the group consisting of triangle, rectangle, oblong, trapezoid, sector and semicircle.

14. The auto-disable safety syringe according to claim 9, wherein said inner cavity of the ring block is provided at the inner wall thereof with one or more spiral grooves, said connecting head is provided at the side wall thereof with one or more protrusions, and cross sections of said spiral grooves and said protrusions having a shape selected from the group consisting of triangle, rectangle, oblong, trapezoid, sector and semicircle.

15. The auto-disable safety syringe according to claim 9, wherein said piston includes a seal plate of said plunger or combination of a piston head with a piston ring of said plunger, and one or more piston grooves, in which said piston ring is embedded, are formed in a side wall of said piston head.

16. The auto-disable safety syringe according to claim 9, wherein a stop sheet capable of being torn is formed at a rear portion of said plunger.

* * * * *